United States Patent
Taniguchi et al.

(10) Patent No.: US 7,125,570 B2
(45) Date of Patent: Oct. 24, 2006

(54) ANTIBACTERIAL COMPOSITION

(75) Inventors: Akio Taniguchi, Nagoya (JP); Yasuo Kurihara, Nagoya (JP); Masashi Uchida, Nagoya (JP)

(73) Assignee: Sinanen Zeomic Co., Ltd., Nagoya (JP)

( * ) Notice: Subject to any disclaimer, the term of this patent is extended or adjusted under 35 U.S.C. 154(b) by 115 days.

(21) Appl. No.: 10/375,114

(22) Filed: Feb. 28, 2003

(65) Prior Publication Data

US 2004/0146567 A1    Jul. 29, 2004

(30) Foreign Application Priority Data

Jan. 23, 2003    (JP)    ............... 2003-015258

(51) Int. Cl.
*A01N 25/22* (2006.01)
*A01N 59/16* (2006.01)
*A01N 59/26* (2006.01)

(52) U.S. Cl. ............ 424/604; 424/618; 424/619; 424/78.09; 424/485; 424/486; 424/487; 514/970; 514/972

(58) Field of Classification Search ........ 424/485–487, 424/618, 619, 78.09, 604; 514/970, 972
See application file for complete search history.

(56) References Cited

U.S. PATENT DOCUMENTS 5,698,229 A * 12/1997 Ohsumi et al. ............ 424/604

2003/0157176 A1 * 8/2003 Nakamura et al. .......... 424/486
2003/0186955 A1 * 10/2003 Vange et al. ................ 514/184

FOREIGN PATENT DOCUMENTS

| JP | 63-265858 | | 11/1988 |
| JP | 11-246213 | | 9/1999 |
| JP | 2000-016904 | * | 1/2000 |

OTHER PUBLICATIONS

Patent Abstracts of Japan, abstracting JP 2001-016904 (2000).*

* cited by examiner

*Primary Examiner*—John Pak
(74) *Attorney, Agent, or Firm*—Oblon, Spivak, McClelland, Maier & Neustadt, P.C.

(57) ABSTRACT

An antibacterial composition is provided which comprises a base, an antibacterial agent consisting of a silver-supporting inorganic compound and a water-soluble salt of a nitrogen atom-containing 6-membered heterocyclic compound. In the antibacterial composition, the silver component susceptible to discoloration is effectively stabilized by the use of the water-soluble salt of a nitrogen atom-containing 6-membered heterocyclic compound and therefore, the antibacterial composition never or hardly undergoes any discoloration with the lapse of time.

12 Claims, No Drawings

ANTIBACTERIAL COMPOSITION

BACKGROUND OF THE INVENTION

The present invention relates to an antibacterial composition and more specifically to an antibacterial composition, which never undergoes any discoloration even with the lapse of time.

In an antibacterial composition comprising an incorporated antibacterial agent, which consists of a silver-supporting inorganic compound, it has been recognized that the incorporated silver component often causes discoloration due to physical actions by, for instance, light rays and heat and/or due to, for instance, a chemical reaction with a substance such as sulfur or a phosphoric acid salt. In this respect, this change may deteriorate the commercial value of a product obtained by processing the composition since the change would result in the formation of such a product, which may partially exhibit a different color in its appearance. Thus, as trials for controlling or eliminating such a color change, there have been proposed a variety of methods such as a method, which makes use of benzotriazole (see, for instance, JP-A-Sho-63-265858) and a method, which makes use of an imide's hydrogen-containing cyclic compound (see, for instance, JP-A-Hei-11-246213). However, these trials have not yet satisfactorily solved the foregoing problem associated with the conventional techniques.

SUMMARY OF THE INVENTION

Accordingly, it is an object of the present invention to provide an antibacterial composition, which never undergoes any discoloration due to, for instance, physical actions such as the action of, for instance, light rays and heat and/or chemical reactions with substances such as sulfur and/or phosphoric acid salts or which can considerably reduce the extent of such discoloration.

According to the present invention, there is thus provided an antibacterial composition, which comprises a base, an antibacterial agent consisting of a silver-supporting inorganic compound and a water-soluble salt of a nitrogen atom-containing 6-membered heterocyclic compound.

DESCRIPTION OF THE PREFERRED EMBODIMENTS

The present invention will hereunder be described in more detail.

In the present invention, the term "an antibacterial agent consisting of a silver-supporting inorganic compound" means an inorganic compound supporting antibacterial silver atom in its stable state. In this respect, examples of such inorganic compounds include zeolite, hydroxyapatite, zirconium phosphate, titanium phosphate, water-containing titanium oxide, hydrotalcite, polyphosphoric acid salts; oxides such as aluminum oxide, iron oxide, silica, water-containing tin oxide, water-containing zirconium oxide and water-containing antimony oxide; hetero-polyacids such as molybdophosphoric acid salts and phosphotungstic acid salts; zeolite (crystalline aluminosilicates); and phosphoric acid salts such as tripolyphosphoric acid salts and hexametaphosphoric acid salts. In this respect, the antibacterial agent consisting of the silver-supporting inorganic compound is preferably one consisting of silver ion-supporting zeolite.

The antibacterial agent consisting of a silver-supporting inorganic compound can easily be prepared by adding an inorganic compound to an aqueous solution of a silver salt, stirring the resulting mixture, separating solids formed therein after the stirring, drying and, if necessary, pulverizing the solids. Examples of silver salts usable herein include silver nitrate and silver sulfate.

In the antibacterial composition of the present invention, the content of the antibacterial agent consisting of a silver-supporting inorganic compound preferably ranges from 0.5 to 6.0% by mass and more preferably 0.7 to 2.5% by mass on the basis of the total mass of the antibacterial composition.

In the present invention, the amount of the silver component present in the antibacterial agent consisting of the silver-supporting inorganic compound ranges from 0.1 to 7.0% by mass and preferably 0.5 to 2.5% by mass on the basis of the total mass of the antibacterial agent.

In this connection, the silver-supporting inorganic compound may likewise comprise other ions, while taking into consideration, for instance, the stability and whiteness of the final composition or processed product. Examples of such other ions are those derived from zinc, copper, calcium, magnesium, potassium, nickel, tungsten, platinum, vanadium, ammonium and amines.

The nitrogen atom-containing 6-membered heterocyclic compound preferably used in the present invention is a compound containing at least two hetero-atoms, at least one of which is nitrogen atom. Specific examples of such 6-membered heterocyclic compounds include pyridazine, pyrimidine, pyrazine, oxazine, thiazine, triazine, oxadiazine, thiadiazine, tetrazine, cyanuric acid, thymine, azathymine, uracil, azauracil, piperazine, phthalhydrazine, phthalazone, barbituric acid, thiouracil, adenine, guanine, xanthine, hypoxanthine, uric acid, theophylline, theobromine and derivatives thereof. Examples of water-soluble salts of nitrogen atom-containing 6-membered heterocyclic compounds include metal salts, for instance, alkali metal salts such as sodium, potassium and lithium salts and alkaline earth metal salts such as calcium and magnesium salts; ammonium salts; and amine salts such as methylamine salt, ethylamine salt, dimethylamine salt, trimethylamine salt, allyl-amine salt and aniline salt.

In this respect, it would be recognized that the water-soluble salt of a nitrogen atom-containing 6-membered heterocyclic compound easily reacts with silver to thus stabilize the same and that, as a result, this permits the effective inhibition of any discoloration of the silver component with the lapse of time, unlike the hardly water-soluble nitrogen atom-containing 6-membered heterocyclic compound in its free state.

The water-soluble salt of a nitrogen atom-containing 6-membered heterocyclic compound used in the present invention can easily be prepared by mixing a nitrogen atom-containing 6-membered heterocyclic compound with a compound capable of forming a salt with the former such as an alkali metal hydroxide, an alkaline earth metal hydroxide, ammonium hydroxide, ammonia or an amine in a solvent. Such a solvent used in the mixing step may be water, a variety of organic solvents (such as alcohols, phenols, ethers, esters, aldehydes, acetals, ketones, hydrocarbons and/or thinner), but is not restricted to any specific one.

Examples of compounds capable of forming salts with nitrogen atom-containing 6-membered heterocyclic compounds include sodium hydroxide, potassium hydroxide, lithium hydroxide, calcium hydroxide, magnesium hydroxide, barium hydroxide, aqueous ammonia, sodium carbonate, potassium carbonate, magnesium carbonate, barium carbonate, ammonium carbonate, sodium nitrate, potassium nitrate, calcium nitrate, magnesium nitrate, ammonium nitrate, sodium sulfate, potassium sulfate, calcium sulfate, magnesium sulfate and ammonium sulfate.

In the present invention, the amount of the water-soluble salt of the nitrogen atom-containing 6-membered heterocyclic compound to be added preferably ranges from 1 to 100% by mass and more preferably 5 to 20% by mass with respect to the amount of the antibacterial agent consisting of the silver-supporting inorganic compound.

Moreover, the content of the water-soluble salt of the nitrogen atom-containing 6-membered heterocyclic compound in the antibacterial composition of the present invention preferably ranges from 0.01 to 2.0% by mass and more preferably 0.05 to 2.0% by mass based on the total mass of the composition.

The base used in the present invention may be, for instance, thermoplastic resins, thermosetting resins, rubber materials, water dispersible paints, organic solvent dispersible paints, oil based paints, cellulose paints, natural polymer-containing adhesives, semi-synthetic polymer-containing adhesives, waxes and inorganic and organic bonds or joint mixtures. Specific examples of such bases are polyethylenes, polypropylenes, polystyrenes, polyesters, polyamides, polyvinyl alcohols, polycarbonates, acrylic resins, silicone resins, polyurethanes, polyester elastomers, polyurethane elastomers, vinyl chloride resins, vinyl acetate resins, fluoroplastics, phenolic resins, melamine resins, urea resins, epoxy resins, alkyd resins, aminoalkyd resins, unsaturated polyester resins, resorcinol resins, rayon, acetates, vinylidene chloride resins, polyethylene terephthalate, gelatin, cellulose, starch, chitosan and gypsum, with the resins being preferably used in the present invention.

The antibacterial composition of the present invention may be molded into a desired shape by, for instance, any conventionally known resin-molding method. Examples of such molding methods usable herein are injection molding, extrusion molding, orientation molding, powder molding, foam molding, roll press molding, cast molding, compression molding, printing and coating.

As has been discussed above in detail, the silver component included in the antibacterial composition of the present invention and susceptible to discoloration due to the action of light rays and/or heat or reactions with, for instance, sulfur and/or phosphoric acid salts is effectively stabilized by the simultaneous use of a water-soluble salt of a nitrogen atom-containing 6-membered heterocyclic compound. Accordingly, the antibacterial composition of the present invention never or hardly undergoes any discoloration with the lapse of time.

EXAMPLES

The present invention will hereunder be described in more detail with reference to the following Examples and Comparative Examples, but the present invention is not restricted to these specific Examples at all.

Preparation Example 1

Antibacterial Composition

To water, there were added various inorganic compounds carrying silver and water-soluble salts of nitrogen atom-containing 6-membered heterocyclic compounds specified in the following Table 1 in the rates likewise specified in Table 1 and the resulting mixture was sufficiently stirred to form a uniform mixture. This mixture was added to a CMC aqueous solution, a starch-containing adhesive or an aqueous emulsion paint with stirring and then the resulting mixture was sufficiently stirred till a uniform mixture was formed. The resulting antibacterial composition was applied onto an aluminum foil of 50 mm×50 mm to a film thickness (determined after drying) of 0.1 mm and then dried at a temperature ranging from 80 to 100° C. for 5 to 12 hours to thus evaluate the susceptibility to discoloration, antibacterial characteristics and anti-fungal characteristics.

Preparation Example 2

Antibacterial Composition

There were admixed various inorganic compounds carrying silver and water-soluble salts of nitrogen atom-containing 6-membered heterocyclic compounds specified in the following Table 1 in the rates likewise specified in Table 1 in a ball mill and the resulting mixture was sufficiently mixed to form a uniform mixture. The resulting mixture was admixed with polypropylene pellets, followed by sufficient mixing to give a uniform mixture. The resulting mixture was molded at 240° C. in an injection molding machine and the resulting shaped antibacterial composition having a size of 50 mm×50 mm×3 mm was used in tests for evaluating the susceptibility to discoloration, antibacterial characteristics and anti-fungal characteristics.

[1. Test for Evaluating Susceptibility of Antibacterial Composition to Discoloration]

The samples prepared in Examples and Comparative Examples were inspected for the discoloration upon irradiation thereof with light rays. In this test, each molded antibacterial composition was exposed to light rays emitted from a 40 W fluorescent tube positioned at a distance of 1 m from the composition at ordinary temperature for 20 days. Each color value in the L*-a*-b* colorimetric system was determined for each sample before and after the foregoing treatment and the color difference ΔE for each sample was calculated. In other words, the susceptibility of each sample to discoloration was expressed in terms of the color difference. The results thus obtained are summarized in the following Table 2.

[2. Tests for Inspecting Antibacterial Composition for Antibacterial and Anti-fungal Characteristics]

The samples prepared in Examples and Comparative Examples were inspected for the antibacterial characteristics and anti-fungal characteristics as follows. More specifically, the test for evaluating antibacterial characteristics was conducted in accordance with JIS Z2801 (bacteria used: *Escherichia coli*), while the test for evaluating the anti-fungal characteristics was conducted in accordance with JIS Z2911. The results thus obtained are likewise listed in the following Table 2.

TABLE 1

| Ex. No. | Ag-supporting inorganic comp. (Ag, Zn or $NH_4^+$ content: % by mass) | Water-soluble salt (part by mass) | Resin (100 parts by mass) |
|---|---|---|---|
| A1 | Ag(6.0)/Zr-phosphate (2.2 pbm) | Potassium salt of uracil (0.3) | CMC |
| A2 | Ag(6.0)/Zr-phosphate (1.7 pbm) | Sodium urate (0.2) | CMC |
| B1 | Ag(2.5)/$NH_4^+$(2.5)/ Zeolite A (1.0 pbm) | Sodium salt of adenine (0.1) | Starch-containing adhesive |

TABLE 1-continued

| Ex. No. | Ag-supporting inorganic comp. (Ag, Zn or $NH_4^+$ content: % by mass) | Water-soluble salt (part by mass) | Resin (100 parts by mass) |
|---|---|---|---|
| B2 | Ag(2.5)/$NH_4^+$/(2.5)/ Zeolite A (0.7 pbm) | Sodium salt of phthalhydrazine (0.05) | Starch-containing adhesive |
| C1 | Ag(2.5)/$NH_4^+$/(2.5)/ Zeolite A (1.0 pbm) | Sodium cyanurate (0.1) | Acrylic aq. emul. type paint |
| C2 | Ag(2.5)/$NH_4^+$/(2.5)/ Zeolite A (1.6 pbm) | Sodium salt of theophylline (0.2) | Acrylic aq. emul. type paint |
| D1 | Ag(1.9)/water-containing titanium oxide (1.4 pbm) | Sodium cyanurate (0.2) | Polypropylene |
| D2 | Ag(1.9)/water-containing titanium oxide (1.4 pbm) | Sodium salt of theophylline (0.2) | Polypropylene |
| E | Ag(2.5)/Zn(14)/ $NH_4^+$(2.5)/Zeolite A (1.0 pbm) | Sodium cyanurate (0.1) | Polypropylene |
| A1* | Ag(6.0)/Zr-phosphate (2.2 pbm) | None | CMC |
| A2* | Ag(6.0)/Zr-phosphate (2.2 pbm) | Uracil (0.3) | CMC |
| A3* | Ag(6.0)/Zr-phosphate (2.2 pbm) | 1,2,3-Benzotriazole (0.3) | CMC |
| A4* | Ag(6.0)/Zr-phosphate (2.2 pbm) | 1,2,4-Benzotriazole (0.3) | CMC |
| B* | Ag(2.5)/$NH_4^+$(2.5)/ Zeolite A (1.0 pbm) | None | Starch-containing adhesive |
| C* | Ag(2.5)/$NH_4^+$(2.5)/ Zeolite A (1.0 pbm) | None | Acrylic aq. emul. type paint |
| D* | Ag(1.9)/water-containing titanium oxide (1.4 pbm) | None | Polypropylene |
| E* | Ag(2.5)/Zn(14)/ $NH_4^+$(2.5)/Zeolite A (1.0 pbm) | None | Polypropylene |

*Comparative Example
Note:
"pbm": part by mass
"CMC": Sodium carboxymethyl cellulose (available from Kishida Chemical Co., Ltd.);
"Starch-containing adhesive": Super Glue 96 α (available from Yazawa Chemical Industry Co., Ltd.);
"Acrylic aq. emul. type paint": KANPE Floor 100 (available from Kansai Paint Co., Ltd.);
"Polypropylene": J707 (available from Grand Polymer Co., Ltd.) to which 0.1% magnesium stearate is added.

TABLE 2

| Ex. No. | Discoloration ($\Delta E$) | Antibacterial Characteristics (value of antibacterial activity) | Anti-fungal property (division for judging) |
|---|---|---|---|
| A1 | 2.0 | Not more than 10 | 0 |
| A2 | 1.3 | Not more than 10 | 0 |
| A1* | 20.8 | 3.6E+01 | 1 |
| A2* | 15.3 | Not more than 10 | 1 |
| A3* | 13.0 | Not more than 10 | 1 |
| A4* | 14.8 | Not more than 10 | 1 |
| B1 | 0.7 | Not more than 10 | 0 |
| B2 | 1.3 | Not more than 10 | 0 |
| B* | 29.7 | 2.0E+01 | 1 |
| C1 | 1.1 | Not more than 10 | 0 |
| C2 | 1.7 | Not more than 10 | 0 |
| C* | 22.5 | 7.0E+01 | 1 |
| D1 | 1.3 | Not more than 10 | 0 |
| D2 | 1.5 | Not more than 10 | 0 |
| D* | 19.6 | 4.0E+02 | 1 |
| E | 12.3 | Not more than 10 | 0 |
| E* | 20.4 | 8.0E+01 | 1 |

*Comparative Example
Note:
The initial number of bacterial cells in the test for evaluating antibacterial characteristics was set at 2.1E+05 (=2.1 × $10^5$) and the number of bacterial cells in the control was set at 2.6E+07 (=2.6 × $10^7$).

What is claimed is:

1. An antibacterial or antifungal composition comprising a base,
   an antibacterial agent consisting of an inorganic compound on which silver ion is supported and
   a water-soluble salt of a nitrogen atom-containing 6-membered heterocyclic compound;
   wherein said inorganic compound is selected from the group consisting of zirconium phosphate, titanium phosphate, and polyphosphoric acid salts;
   wherein the nitrogen atom-containing 6-membered heterocyclic compound is a member selected from the group consisting of pyridazine, pyrimidine, pyrazine, oxazine, thiazine, triazine, oxadiazine, thiadiazine, tetrazine, cyanuric acid, thymine, azathymine, uracil, azauracil, piperazine, phthalhydrazine, phthalazone, barbituric acid, thiouracil, adenine, guanine, xanthine, hypoxanthine, uric acid, theophylline, theobromine and derivatives thereof; and
   wherein the water-soluble salt is a member selected from the group consisting of metal salts; ammonium salts; and amine salts.

2. The antibacterial or antifungal composition of claim 1, wherein the content of the antibacterial agent consisting of an inorganic compound on which silver is supported in the composition ranges from 0.5 to 6.0% by mass on the basis of the total mass of the antibacterial composition.

3. The antibacterial or antifungal composition of claim 2, wherein the content of the antibacterial agent consisting of an inorganic compound on which silver ion is supported in the composition ranges from 0.7 to 2.5% by mass on the basis of the total mass of the antibacterial composition.

4. The antibacterial or antifungal composition of claim 1, wherein the amount of silver in the antibacterial agent consisting of an inorganic compound on which silver ion is supported ranges from 0.1 to 7.0% by mass on the basis of the total mass of the antibacterial agent.

5. The antibacterial or antifungal composition of claim 1, wherein the content of the water-soluble salt ranges from 0.01 to 2.0% by mass on the basis of the total mass of the composition.

6. The antibacterial or antifungal composition of claim 5, wherein the content of the water-soluble salt ranges from 0.05 to 2.0% by mass on the basis of the total mass of the composition.

7. The antibacterial or antifungal composition of claim 1, wherein the amount of the water-soluble salt ranges from 1 to 100% by mass relative to that of the inorganic compound on which silver ion is supported.

8. The antibacterial or antifungal composition of claim 7, wherein the amount of the water-soluble salt ranges from 5 to 20% by mass relative to that of the inorganic compound on which silver ion is supported.

9. The antibacterial or antifungal composition of claim 1, wherein the base is selected from the group consisting of polyethylenes, polypropylenes, polystyrenes, polyesters, polyamides, polyvinyl alcohols, polycarbonates, acrylic resins, silicone resins, polyurethanes, polyester elastomers, polyurethane elastomers, vinyl chloride resins, vinyl acetate resins, fluoroplastics, phenolic resins, melamine resins, urea resins, epoxy resins, alkyd resins, aminoalkyd resins, unsaturated polyester resins, resorcinol resins, rayon, acetates, vinylidene chloride resins, polyethylene terephthalate, gelatin, cellulose, starch, chitosan and gypsum.

10. The antibacterial or antifungal composition of claim 1, wherein the base is a resin.

11. The antibacterial or antifungal composition of claim 1, wherein the base is selected from the group consisting of a carboxymethyl cellulose, a starch-containing adhesive, a polypropylene, and mixtures thereof.

12. The antibacterial or antifungal composition of claim 1, wherein said inorganic compound is selected from the group consisting of zirconium phosphate, and titanium phosphate.

* * * * *